United States Patent [19]

Lev et al.

[11] 4,034,286
[45] July 5, 1977

[54] DEVICE FOR DETECTING A FAILURE IN AN INSULATION SYSTEM

[75] Inventors: Yaacov Lev, Liverpool, England; Frederick R. Pritchard, Caergwrle, nr. Wrexham, Wales

[73] Assignee: Shell Internationale Research Maatschappij B.V., Netherlands

[22] Filed: Nov. 3, 1975

[21] Appl. No.: 628,059

[52] U.S. Cl. .............................. 324/71 R; 340/234; 73/342
[51] Int. Cl.² .................................... G01N 27/00
[58] Field of Search ................ 324/71 R, 62, 65 R; 73/342, 45.2; 340/227, 228, 234, 242

[56] References Cited
UNITED STATES PATENTS

| 3,484,805 | 12/1969 | Lorenz | 340/234 |
| 3,665,766 | 5/1972 | Johnston | 73/342 |
| 3,914,688 | 10/1975 | Lev | 324/71 R |

Primary Examiner—Rudolph V. Rolinec
Assistant Examiner—Michael J. Tokar
Attorney, Agent, or Firm—Pravel, Wilson & Gambrell

[57] ABSTRACT

An apparatus for detecting a leak in an insulation system utilizing a plurality of sensing devices disposed in a grid-like arrangement in heat transfer relationship to the insulation. Each sensing device comprises a small enclosed chamber filled with an ion-conducting material that solidifies when subjected to the temperature produced by a leak in the insulation and changes conductivity. The conductivity of the sensing devices is monitored to detect leaks in the insulation.

4 Claims, 4 Drawing Figures

DEVICE FOR DETECTING A FAILURE IN AN INSULATION SYSTEM

CROSS-REFERENCE TO RELATED APPLICATION

The present invention is related to the invention described and claimed in application Ser. No. 402,555, filed Oct. 1, 1973 by Y. Lev and entitled "Cold Spot Detector For LNG Tanks And Tankers".

BACKGROUND OF THE INVENTION

The present invention relates to a device for detecting a failure in an insulation system, in particular in the insulation system of a cryogenic tank.

The device according to the above-referenced earlier patent application comprises an electrically non-conducting conduit containing an ion-conducting material which will solidify at low temperature and which has a different conductivity when solid, said conduit having at alternate ends thereof, in contact with said ion-conducting material, a pair of electrodes externally connected together in such a manner as to facilitate measurement of the ionic-conductivity of said ion-conducting material, and means to monitor the ionic-conductivity of said ion-conducting material, said monitoring means being adapted to be placed in electrical connection with said electrodes.

BRIEF SUMMARY OF THE DISCLOSURE

The improved device according to the present invention comprises at least one cellular unit containing an ion-conducting material, which will solidify at low temperature and which has a different conductivity when solid, and having at alternate ends thereof, in contact with said ion-conducting material, a pair of electrodes externally connected together in such a manner as to facilitate measurement of the ionic-conductivity of said ion-conducting material, and means to monitor the ionic-conductivity of the ion-conducting material, said monitoring means being adapted to be placed in electrical connection with said electrodes.

Preferably, a plurality of said cellular units is circuited in a group, for example, in series.

The main difference between the device according to the present invention and the device according to the above referenced earlier patent application is that instead of non-conducting conduits of relatively great length containing an ion-conducting material, cellular units are used which contain the said ion-conducting material.

The cellular units have the advantage that, since they are individual discrete units, they can be mounted in any desired geometry on or within an insulation system and thus can be concentrated in areas of special interest. Furthermore, these cellular units can be circuited in series to monitor a similar area as the conduit of relatively great length according to the earlier application, while having a much lower initial electrical resistance. Finally, the cellular units can easily be encapsulated within a film or layer of plastic or other suitable material for use in areas where they might be subjected to salt water or other abuse.

BRIEF DESCRIPTION OF THE DRAWINGS

The invention will be further explained with reference to the attached drawings, wherein.

PREFERRED EMBODIMENTS

Figure 1:
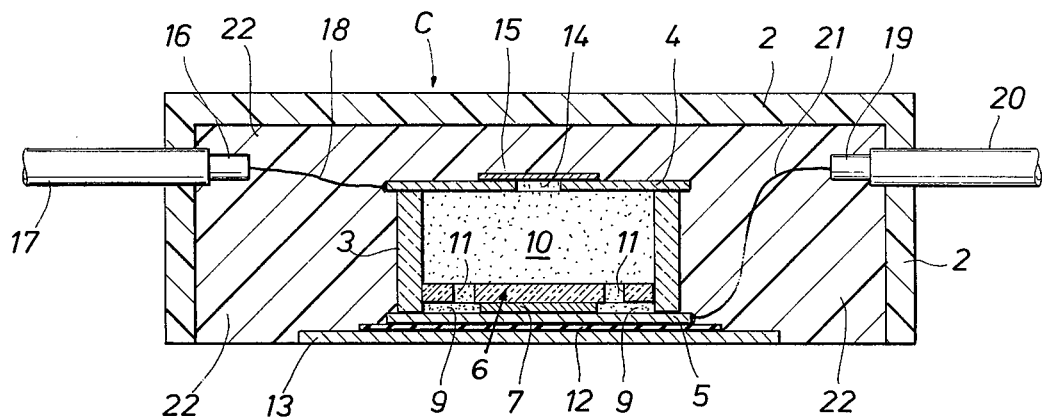
FIG. 1 shows a side view of a cross-section of one embodiment of the cellular unit according to the invention.

The cellular unit C as shown in FIG. 1 comprises an outer housing 2 made of a suitable material such as for example polyvinylchloride. Within the housing 2 a tubular element 3 is arranged, which is made of a suitable electrically insulating material, such as for example glass. Disc-shaped metal (for example copper) electrodes 4 and 5 are secured to both ends of the tubular element 3, so that the interior volume 10 of the tubular element 3 is closed in a gas- and liquid-tight manner. Within the tubular element 3, a transverse wall 6 made of a suitable thermal insulating material, such as for example polyvinylchloride, is arranged at a short distance from the electrode 5 and a relatively small metal (for example copper) spacer disc 7 being arranged between the elements 5 and 6. The thermal insulator 6 is provided with a number of openings 11. The elements 3, 5, 6 and 7 enclose a relatively small annular space or reservoir 9. Furthermore, the elements 3, 4 and 6 enclose a cylindrical shaped interior volume or reservoir 10, which is relatively large compared with reservoir 9. During manufacture of the cellular unit C, the reservoirs 10 and 9, which communicate with each other via the openings 11, are filled through an opening 14 in electrode 4 with a suitable ion-conducting material, for example a brine solution (NaCl in water). After the filling of said reservoirs 9 and 10, the opening 14 is closed by means of a small metal (for example copper) disc 15 which is secured to the electrode 4 in a gas- and liquid-tight manner.

An electrical insulating layer 12, for example made of another suitable plastic, is secured to the electrode 5 and against the layer 12 a disc-shaped metal (for example copper) thermal conductor 13 is secured. A cable 16 which is adapted to conduct electricity and is provided with electrical insulation 17, is electrically connected by means of a metal wire 18 to the electrode 4. Another cable 19, which is adapted to conduct electricity and which is provided with electrical insulation 20, is electrically connected by means of a metal (copper) wire 21 to electrode 5. The remaining space 22 within the housing 2 is filled with a suitable sealing compound, for example with an epoxy resin.

Figure 3:
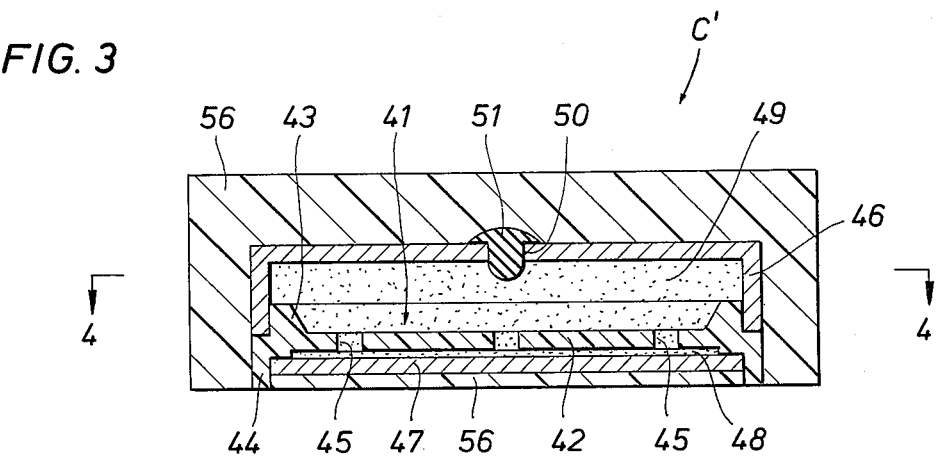
FIG. 3 shows a cross-section taken along line III-III of FIG. 4 of a second embodiment of the cellular unit according to the invention.
Figure 4:
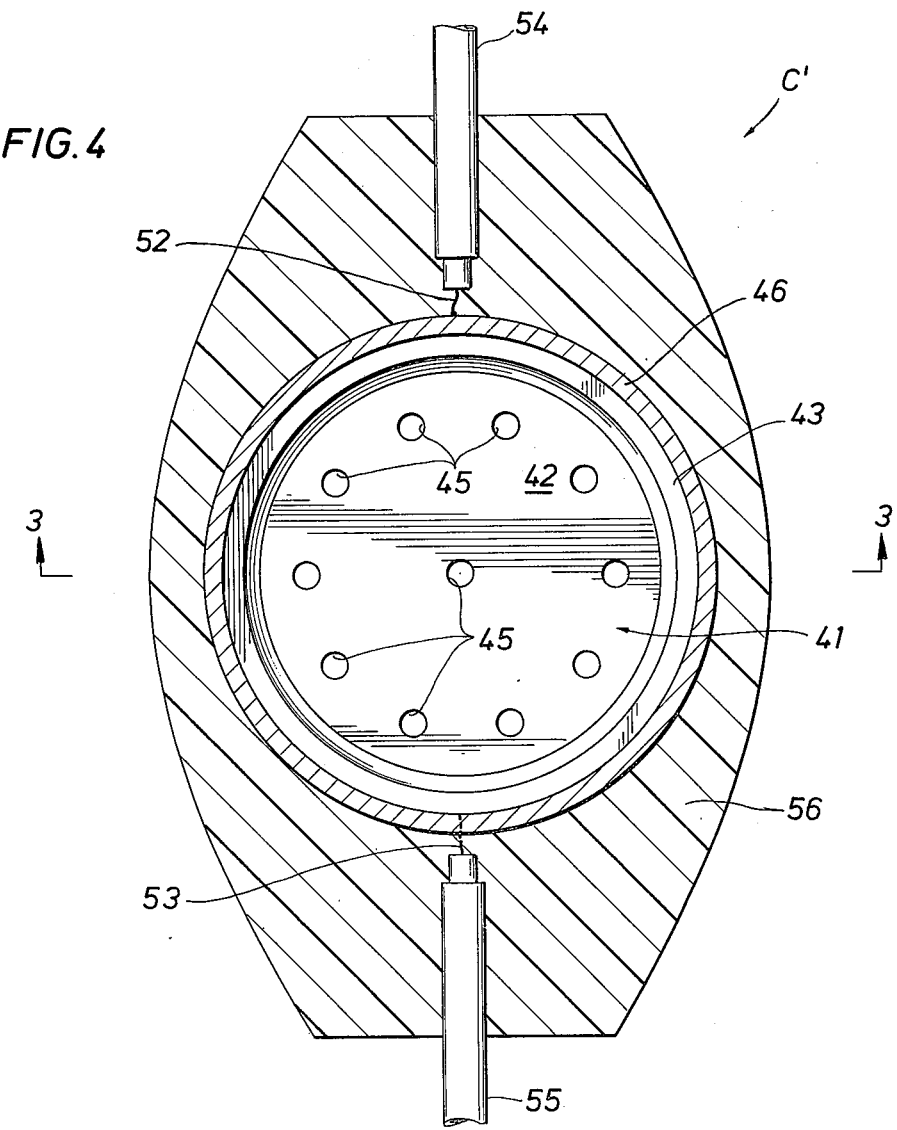
FIG. 4 shows a plan view of the second embodiment of the cellular unit.

The embodiment of the cellular unit C' as shown in FIGS. 3 and 4 is basically the same as the cellular unit C as shown in FIG. 1. It is however, so designed that it comprises only a small number of parts, so that it is particularly suitable for production in large quantities.

A transverse wall 41, made as one piece and moulded of a suitable plastic material, for example polyvinylchloride, consists of a disc-shaped part 42, having a large number of openings 45. The element 41 is provided with flanges 43 and 44 on opposite sides of said disc-shaped part 42 with the flanges acting as a thermal insulator. A metal (preferably copper) cup 46 is fitted in a gas- and liquid-tight manner on the flange 43, said metal cup 46 forming one of the electrodes of the cellular unit. A metal disc 47 is fitted in a gas- and liquid-tight manner within the flange 44, said metal disc 47 forming the other electrode of the cellular unit. The elements 42 and 47 enclose a relatively small volume or reservoir 48. Furthermore, the elements 42, 43 and 46 enclose a volume or reservoir 49, which is relatively large compared with reservoir 48. Both reservoirs 48 and 49 communicate with each other via the openings 45. During manufacture of the unit the reservoirs 48 and 49 are filled through an opening 50 in electrode 46 with a suitable ion-conducting material, for example a brine solution (NaCl in water). After filling of the reservoirs 48 and 49, the opening 50 is closed by means of a rubber sealing plug 51. Each electrode 46 and 47 is provided with a corresponding insulated electrical lead 52 and 53 as shown in FIG. 4.

In order to protect the cellular unit C' against water and mechanical damage, it is encapsulated within a suitable plastic material 56, for example a suitable epoxy resin.

Figure 2:
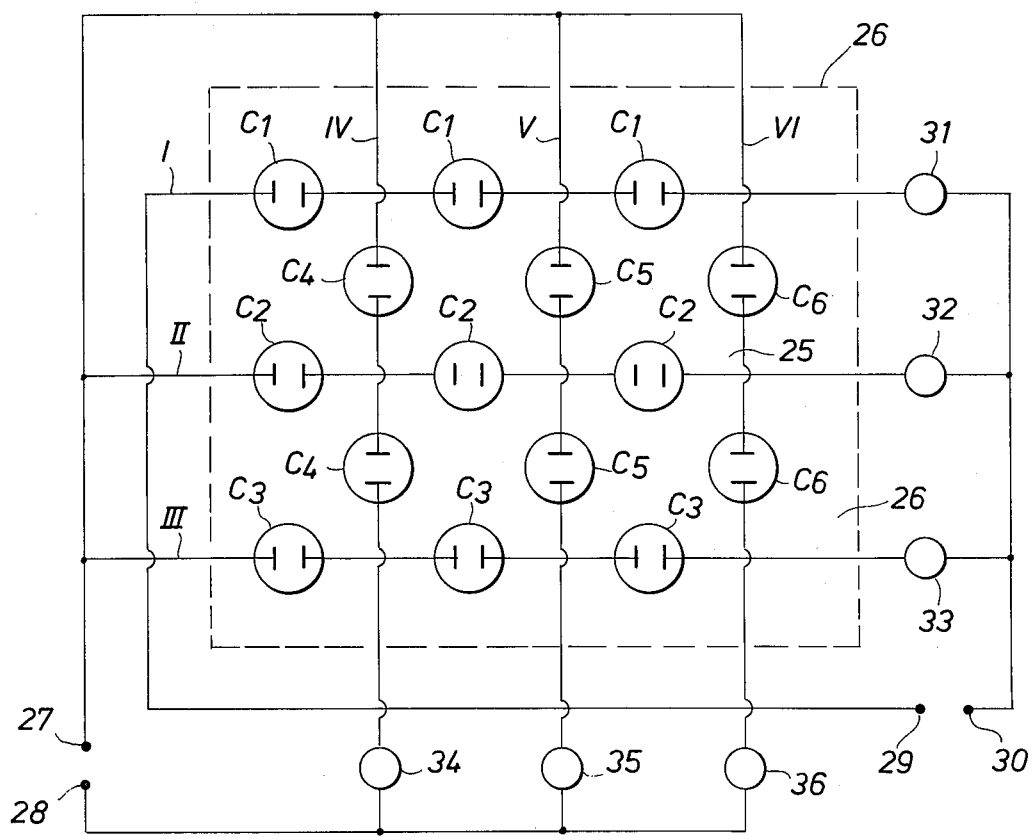
FIG. 2 shows schematically an arrangement of a plurality of the cellular units according to the invention.

In FIG. 2 the use of a number of groups of the cellular units C or C' according to the invention is shown schematically. Referring to FIG. 2, a number of cellular units, respectively $C_1$, $C_2$, $C_3$, $C_4$, $C_5$ and $C_6$ are each circuited in series so that they form respectively the groups I, II, III, IV, V and VI.

If the cellular unit C according to FIG. 1 is used, the disc-shaped metal thermal conductor 13 of the cellular unit will be in heat transfer contact with the insulating system 26 (schematically indicated by the dotted lines). For example with the outer surface of the inner hull of a tanker for liquefied natural gas, or embedded in the insulating material of the insulating system. If the cellular unit C' according to FIGS. 3 and 4 is used, the surface at the left hand side of the unit as shown in FIG. 3 will be arranged in heat transfer contact with the insulating system 26.

The groups I, II, III, IV, V and VI are each provided with a device for indicating a change in the magnitude of the electric current, said devices being indicated respectively by the reference numerals 31, 32, 33, 34, 35 and 36.

OPERATION

Terminals 27 and 28 of a pair and terminals 29 and 30 of another pair are each connected to a source of electric power (AC or DC). If no failure is present, a certain predetermined electric current will pass through the cellular units of each group. When a failure develops in the insulation system, for example at the location indicated by reference numeral 25, a cold spot will develop at said location. The drop in temperature will cause the ion-conducting material in the small reservoir 9 (if unit C according to FIG. 1 is used) or in the small reservoir 48 (if unit C' according to FIGS. 3 and 4 is used) in each cellular unit $C_2$ and $C_6$ which is closest to the location 25 to solidify. This will cause a change (normally a drop) in the magnitude of the current passing through group II and group VI. The corresponding devices 32 and 36 will detect this change and will cause a suitable warning device (for example optical or acoustical) to start operation. Then the existence of a failure and its location will be known to the personnel operating the device.

The above scheme discloses a possible arrangement of the cellular units according to the invention. It will be clear that other arrangements are possible. It is, for example, possible to arrange the cellular units in a pattern consisting of a number of concentric circles.

Furthermore, it is remarked that the use of an outside source of electric power is not strictly necessary. It is, for example, possible to use in each cellular unit a pair of electrodes, wherein one electrode of a pair is made of a metal different from the metal of the other electrode of said pair (for example one electrode made of zinc and one electrode made of copper), so that an electric current can be generated in the cellular unit. In that case the terminals 27 and 28 have to be electrically interconnected. The same applies to the terminals 29 and 30. Upon solidification of the ion-conducting material in one or more cellular units, the magnitude of the electric current will change in substantially the same way as described in the above.

The use of the small reservoirs 9 and 48 in the cellular units C and C' has the advantage that a great sensitivity of the device is obtained. The purpose of the large reservoirs 10 and 49 is to compensate for possible losses (for example by evaporation or diffusion) of the ion-conducting material. This is desirable since the cellular units, if for example installed in a tanker for transport of liquefied natural gas, must have a long useful life, for example about 20 years.

Examples of suitable ion-conducting materials are solutions of various salts in water, for example NaCl in water or copper sulfate in water (in combination with copper electrodes). Furthermore, it is possible to use hydrates of organic chemical compounds as ion-conducting material.

We claim as our invention:

1. A sensing device for detecting a failure in an insulation system of cryogenic tank comprising:
   a closed housing;
   a pair of spaced electrodes mounted within said housing;
   a pair of electrical leads, one of said leads being attached to each of said electrodes;
   said housing being filled with an ion-conducting material that solidifies when subjected to the temperature produced by a leak in the insulation, said ion-conducting material changing conduction upon solidifying; and
   said housing having a transverse wall disposed to divide the interior of the housing into two reservoirs of unequal volumes, said reservoirs being in fluid communication, and said electrodes being disposed on opposite sides of said transverse wall.

2. The sensing device of claim 1, wherein said housing is cylindrical and said transverse wall is substantially parallel to the ends of the cylinder and one of said reservoirs being considerably smaller than the other.

3. A sensing device for detecting a failure in an insulation system of cryogenic tank comprising:
   a closed housing;
   a pair of spaced electrodes mounted within said housing;
   a pair of electrical leads, one of said leads being attached to each of said electrodes;
   said housing being filled with an ion-conducting material that solidifies when subjected to the temperature produced by a leak in insulation, said ion-conducting material changing conduction upon solidifying; and
   said housing having a wall disposably dividing the interior of the housing into two or more reservoirs of unequal volumes, said reservoirs being in fluid communication, and said electrodes being disposed on opposite sides of said transverse wall.

4. The sensing device of claim 3, wherein:
said housing and transverse wall within are cylindrical and said transverse wall is substantially parallel to the ends of the cylinder and one of said reservoirs being considerably smaller than the others; and
said reservoirs are in fluid communication through numerous openings each having a substantially smaller diameter than the diameter of the transverse wall.

* * * * *